United States Patent [19]

Iizuka et al.

[11] Patent Number: 4,607,117

[45] Date of Patent: Aug. 19, 1986

[54] METHYL 2-(2-HYDROPEROXY-2-PROPYL)NAPHTHALENE-6-CARBOXYLATE AND PROCESS FOR PRODUCING THE SAME

[75] Inventors: Akira Iizuka; Yutaka Konai; Takashi Yamauchi; Shoichiro Hayashi, all of Iwaki, Japan

[73] Assignee: Kureha Kagaku Kogyo Kabushiki Kaisha, Tokyo, Japan

[21] Appl. No.: 731,055

[22] Filed: May 6, 1985

[30] Foreign Application Priority Data

May 17, 1984 [JP] Japan ................................. 59-99383

[51] Int. Cl.$^4$ ............................................. C07C 69/76
[52] U.S. Cl. ......................................... 560/56; 562/467
[58] Field of Search ............................ 560/57; 562/467

[56] References Cited

U.S. PATENT DOCUMENTS 2,776,322  1/1957  Webster et al. ...................... 260/621

OTHER PUBLICATIONS

Louw, R. J.A.CS 97(15) 4396-7, 1975.

*Primary Examiner*—Paul J. Killos
*Attorney, Agent, or Firm*—John P. White

[57] ABSTRACT

Disclosed herein are methyl 2-(2-hydroperoxy-2-propyl)naphthalene-6-carboxylate represented by the formula (I):

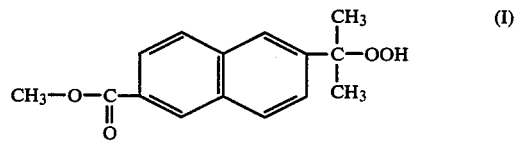

and a process for producing the compound represented by the formula (I) at a high purity and in a high yield.

6 Claims, 3 Drawing Figures

METHYL 2-(2-HYDROPEROXY-2-PROPYL)NAPHTHALENE-6-CARBOXYLATE AND PROCESS FOR PRODUCING THE SAME

BACKGROUND OF THE INVENTION

The present invention relates to methyl 2-(2-hydroperoxy-2-propyl)naphthalene-6-carboxylate represented by the formula(I):

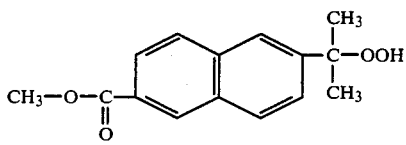

and a process for producing the same. More in detail, the present invention relates to methyl 2-(2-hydroperoxy-2-propyl) naphthalene-6-carboxylate represented by the formula(I), which is an intermediate compound for producing 2-hydroxynaphthalene- 6-carboxylic acid that is useful as a raw material for producing highpolymeric materials, and to a process for producing methyl 2-(2-hydroperoxy-2-propyl)naphthalene-6-carboxylate at a high purity and in a high yield.

Because of the excellent properties such as high elasticity, high tensile strength and high heat-resistance of the polymeric materials obtained from 2-hydroxynaphthalene-6-carboxylic acid (hereinafter referred to as "acid-6"), acid-6 has attracted the attention as a raw material for fibers and other shaped goods in recent years.

Hitherto, as a process for producing acid-6, the following processes have been known.

(i) A process in which potassium salt of beta-naphthol is reacted with gaseous carbon dioxide at a high temperature and under a pressure (refer to U.S. Pat. Nos. 1,593,816; 4,287,357; 4,345,095; 4,329,494 and 4,345,094), (ii) A process in which potassium salt of beta-naphthol is reacted with gaseous carbon dioxide in a high-boiling medium at a high temperature and under a pressure(refer to Japanese Patent Applications Laying-Open Nos. 57-95939 and 58-99436) and (iii) A process in which 6-bromo-2-naphthol is reacted with carbon monoxide in methanol.

However, there are the following demerits in the above-mentioned processes.

Namely, in the processes (i) and (ii), it is necessary to carry out the reaction at a high temperature between 260° and 280° C., and in the process (iii), it is necessary to carry out the reaction under a high pressure of about 70 kg/cm$^2$. As a result, in these processes a special apparatus is required because of the high reaction temperature or pressure.

In addition, because of the by-production of a large amount of beta-naphthol in the processes (i) and (ii), it is necessary to separate the by-produced beta-naphthol from the reaction product, and as a result the process complicates. Besides, in the processes (i) and (ii), the by-production of 2-hydroxynaphthalene-3-carboxylic acid as one of the isomers of the objective compound (acid-6) is unavoidable and the separation of the by-product from the reaction product is difficult. Such by-production causes a problem of lowering the reaction selectivity.

In addition to the above-mentioned demerits, the yield of acid-6 in the known processes is low, that is, about 26.5%, 45% and 37% in the process (i), (ii) and (iii), respectively and accordingly, the known processes are not adequate as an industrial process.

In consideration of the above-mentioned situations, the present inventors have studied the industrially profitable processes for producing acid-6, and as a result, have found that acid-6 is produced at a high purity in an excellently high yield by subjecting the novel compound, methyl 2-(2-hydroperoxy-2-propyl)naphthalene-6-carboxylate to acid-decomposition and hydrolysis, and based on this finding, the present inventors have succeeded in dissolving the problems of the above-mentioned conventional processes for producing acid-6 and thus attained the present invention.

SUMMARY OF THE INVENTION

In the first aspect of the present invention, there is provided methyl 2-(2-hydroperoxy-2-propyl)naphthalene-6-carboxylate represented by the formula (I):

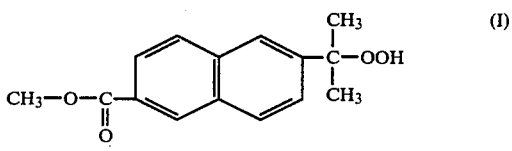

In the second aspect of the present invention, there is provided a process for producing methyl 2-(2-hydroperoxy-2-propyl)naphthalene-6-carboxylate, comprising reacting methyl 2-isopropylnaphthalene-6-carboxylate with oxygen at a temperature of 70° to 120° C. in an aqueous alkali solution of pH 8 to 13 in the presence of 0.005 to 0.5% by weight of a catalyst comprising a cobalt or manganese salt of an organic acid to the amount of the methyl 2-isopropylnaphthalene-6-carboxylate.

BRIEF DESCRIPTION OF THE DRAWINGS:

Of the attached drawings.

Figure 1:
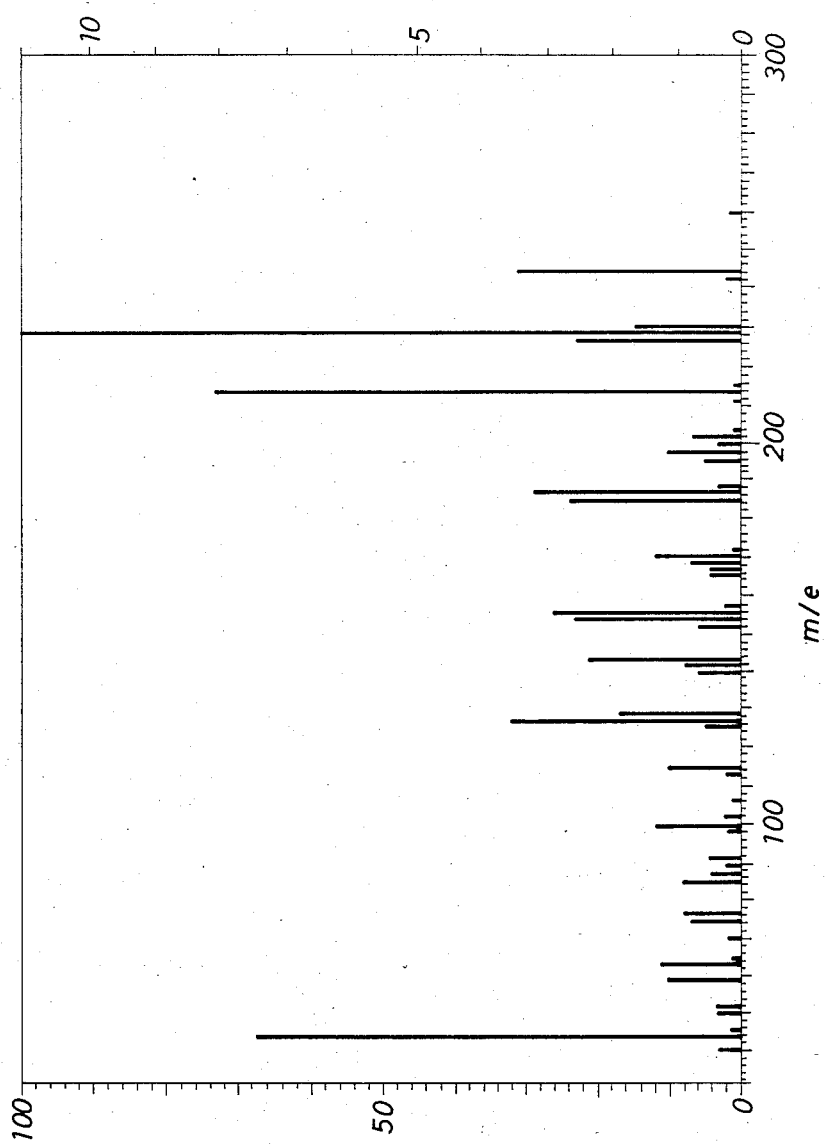
FIG. 1 shows a mass spectrum of methyl 2-(2-hydroperoxy-2-propyl)naphthalene-6-carboxylate.

DETAILED EXPLANATION OF THE INVENTION:

The present invention relates to the novel compound, methyl 2-(2-hydroperoxy-2-propyl)naphthalene-6-carboxylate (hereinafter referred to as "the present compound") represented by the formula(I):

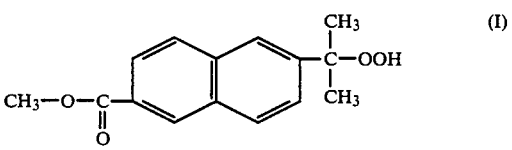

and the process for producing the present compound by reacting methyl 2-isopropylnaphthalene-6-carboxylate with oxygen in an aqueous alkali solution in the presence of a catalyst comprising a cobalt or manganese salt of an organic acid under heating. The present compound is obtained in a highly pure state by the purification process in which the obtained reaction product containing the present compound is cooled to precipitate crystals and the thus precipitated powdery crystals are collected followed by washing the crystals with an aliphatic hydrocarbon solvent to obtain the present compound.

Namely, the present compound is produced by the following process.

Methyl 2-isopropylnaphthalene-6-carboxylate (hereinafter referred to as "methyl ester") is added to an aqueous alkali solution (pH 8 to 13) of the amount of 1 to 10 times by weight, preferably 2 to 3 times by weight of methyl ester, and methyl ester is reacted with oxygen in an atmospheric pressure or under a pressure at a temperature of from 70° to 120° C., preferably from 80° to 95° C. in the presence of a catalyst comprising a cobalt or manganese salt of an organic acid in an amount of 0.005 to 0.5%, preferably 0.02 to 0.1% by weight of methyl ester while blowing an oxygen-containing gas into the thus mixed solution and stirring the mixed solution for 10 to 30 hours. On cooling the thus obtained reaction mixture by the above-mentioned reaction, the present compound precipitates with the starting material and by-products as crystals, and the present compound can be obtained by collecting the crystals and subjecting thereof to purification.

In the process, as the aqueous alkali solution, those of sodium carbonate, sodium hydrogencarbonate and borax may be exemplified, and as the cobalt or manganese salt of an organic acid, cobalt naphthenate, manganese naphthenate and the like may be exemplified.

In addition, on carrying out the reaction, it is preferable that an organic peroxide such as benzoyl peroxide or azobisisobutyronitrile in an amount of from 0.1 to 5% by weight of methyl ester is added into the aqueous solution for reducing the reaction time.

Furthermore, in the process wherein methyl ester is reacted with oxygen in an aqueous alkali solution to be oxidized into the present compound, the influence of the pH of the aqueous solution on the reaction rate is important, and in the case where the pH is lower than 8 or over 13, the reaction is slow and the production of by-products increases and accordingly, the pH of the aqueous solution is adjusted to pH 8 to 13, preferably from 9 to 12.

By the way, methyl 2-isopropylnaphthalene-6-carboxylate used as the starting material is easily available by esterifying 2-isopropyl nephthalene-6-carboxylic acid with an excess methanol in the presence of an acid catalyst.

The composition of the crystals obtained by precipitating the reaction mixture formed in the reaction of methyl ester and oxygen, varies according to the reaction conditions, for instance, after carrying out the reaction for 20 to 30 hours, the composition comprises 75 to 85% by weight of the present compound, 10 to 20% by weight of the unreacted starting material and less than about 5% by weight of the other substance(s) (as a result of analysis by high pressure liquid chromatography). The result shows the excellent reaction selectivity of the present compound in the process according to the present invention.

The method of purification for obtaining the present compound of a high purity from the thus collected powdery crystals mainly containing the present compound comprises the step of washing the powdery crystals with an aliphatic hydrocarbon solvent, preferably with stirring at room temperature. Since methyl 2-isopropylnaphthalene-6-carboxylate contained in the crystals dissolves in the aliphatic hydrocarbon solvent, but the present compound also contained in the crystals does not dissolved in the solvent, it is possible to obtain the present compound of a purity higher than 98% in a high yield by the above-mentioned purification method.

Accordingly, as the aliphatic hydrocarbon solvents, solvents which dissolve selectively methyl 2-isopropylnaphthalene-6-carboxylate can be used in the purification, and for instance, n-hexane, n-heptane and the like may be exemplified.

In addition, since the unreacted methyl 2-isopropylnaphthalene- 6-carboxylate can be recovered in a highly pure state by the above-mentioned purification step, the thus recovered methyl ester can be reused as the starting material in the above-mentioned synthetic process, and thereby it is possible to raise the yield of the present compound furthermore.

The thus obtained present compound has been confirmed as the compound of a molecular formula of $C_{15}H_{16}O_4$ represented by the formula (I) by the elementary analytical data and the spectroscopic data, and shows the following physicochemical properties.

(i) Molecular weight: 260.3
(ii) Appearance: colorless plate-like crystal
(iii) Melting point: 92°–93° C.
(iv) Solubility: soluble in acetone, ethanol, benzene, ether, chloroform and acetonitrile and insoluble in n-hexane, n-heptane and water
(v) Elementary analytical data:

|  | C (%) | H (%) |
| --- | --- | --- |
| found: | 69.10 | 6.35 |
| calcd. as $C_{15}H_{16}O_4$: | 69.21 | 6.20 |

Figure 2:
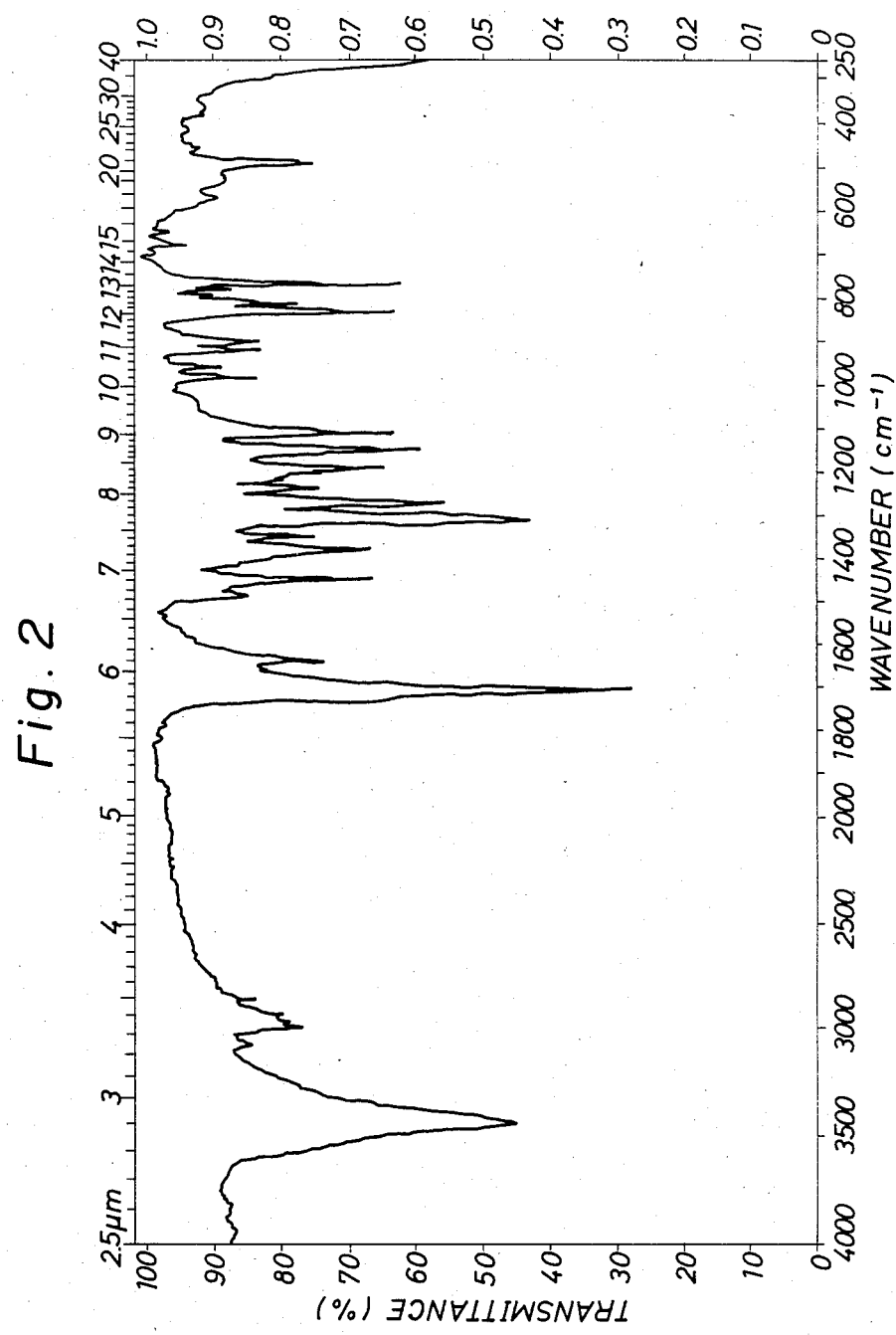
FIG. 2 shows an infrared absorption spectrum of methyl 2-(2-hydroperoxy-2-propyl)naphthalene-6-carboxylate and FIG. 3 shows a $^1$H-nuclear magnetic resonance spectrum of methyl 2-(2-hydroperoxy-2-propyl)naphthalene-6-carboxylate.
Figure 3:
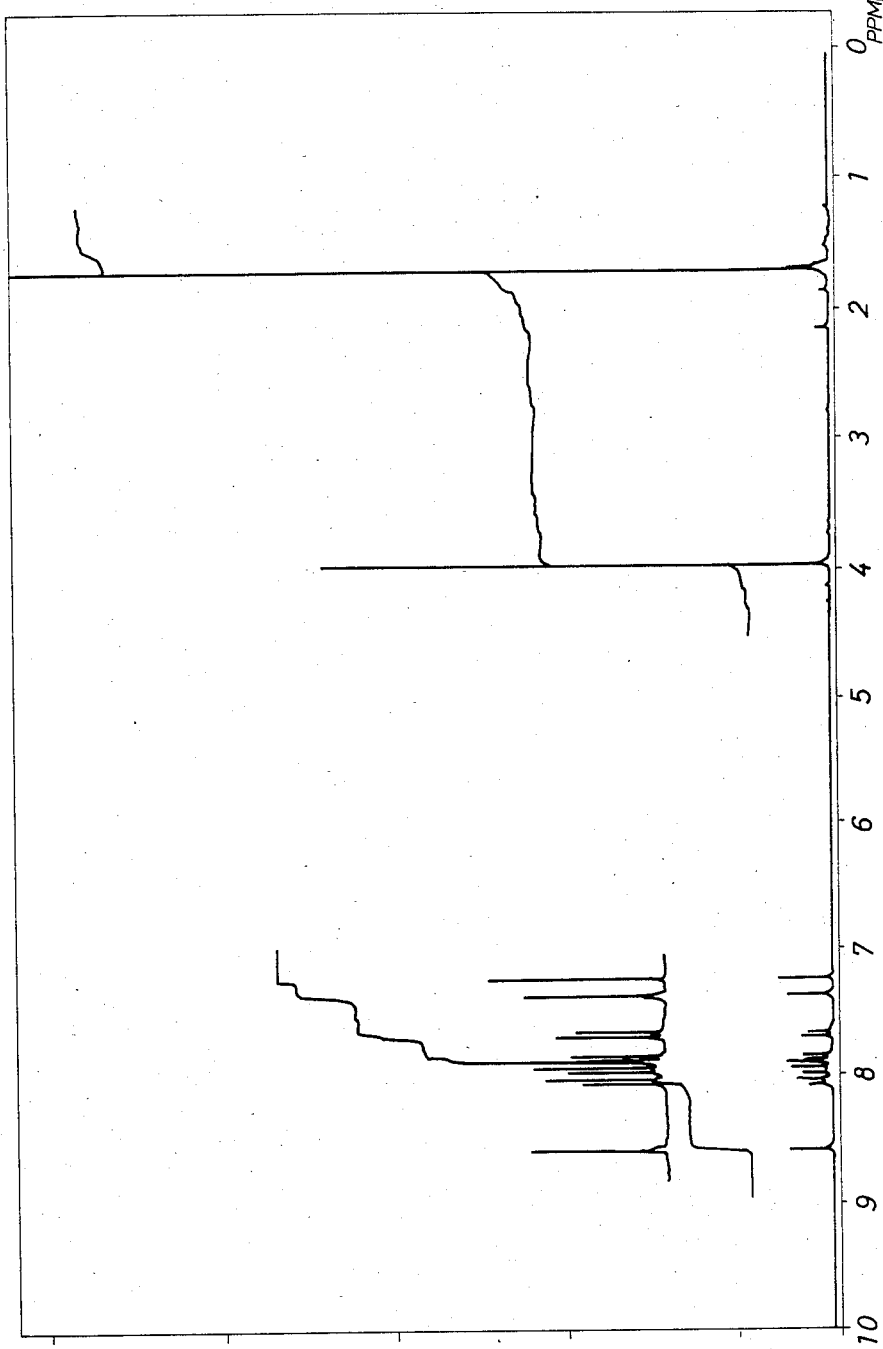

(vi) Mass spectral analytical data: $M^+ = 260$ (Electron-Impact-MS, ionization voltage: 70 V) (refer to the mass spectrum shown in FIG. 1)
(vii) Infrared absorption spectrum: (refer to FIG. 2)
(viii) $^1H$ Nuclear magnetic resonance spectrum: (refer to FIG. 3 taken under 250 MHz in $CDCl_3$)

As has been described above, the present compound as a novel compound is obtained in a highly pure state and in a high yield by the process according to the present invention.

In addition, as has been shown above, the present compound melts at 92°–93° C., and is a stable and colorless plate-like crystalline hydroperoxide not decomposed even when heated to 120° C., and is soluble in a number of organic solvents such as acetone, ethanol and chloroform, and namely, the present compound is a peroxide which is extremely easy to handle.

In this connection, a hydroperoxide such as t-butyl hydroperoxide, cumene hydroperoxide and diisopropylbenzene hydroperoxide is not only sensitive to impact and friction but also it is extremely inflammable and instantly burns or explodes and accordingly, it is necessary to take care on handling such a hydroperoxide, and such a hydroperoxide can hardly be used as an industrial raw material.

However, in spite of being a hydroperoxide, the present compound has surprisingly different property from the conventional hydroperoxide, namely, the present compound does not decompose even when heated to 120° C. and it is a compound which is extremely stable and easy to handle.

In the case where 1.0 g of the present compound, methyl 2-(2-hydroperoxy-2-propyl)naphthalene-6-carboxylate are heated in 10.0 g of acetone for 30 min at a temperature between 50° and 70° C. in the presence of 0.02 g of sulfuric acid as a catalyst, methyl 2-hydroxynaphthalene-6-carboxylate is formed nearly quantitatively. The thus formed compound is hydrolyzed nearly quantitatively into 2-hydroxynaphthalene-6-carboxylic acid (acid-6) by heating the thus formed compound for 30 min at a temperature between 20° and 50° C. in an aqueous about 1N alkali solution.

Namely, the present compound is an extremely favorable hydroperoxide as a raw material for industrially producing acid-6.

In addition, since the present compound can be obtained in a highly pure state and in a high yield according to the process of the present invention, the present process is highly favorable as an industrial process for producing the present compound, methyl 2-(2-hydroperoxy-2-propyl) naphthalene-6-carboxylate.

Although one skilled in the art can easily ascertain the essential characteristics of the present invention from the foregoing description, the present invention will be explained in more detail while referring to the following non-limitative examples.

EXAMPLE 1

In a separable glass flask of a capacity of 200 ml, provided with a turbine stirrer, a reflux condesner, an inlet tube for blowing a gas and a thermometer, 20 g (0.0877 mol) of methyl 2-isopropylnaphthalene-6-carboxylate, 80 ml of water, 0.2 g of benzoyl peroxide, 0.64 g of sodium carbonate and 12 mg of cobalt naphthenate were introduced, and peroxidation was carried out while heating the content of the flask at 90° C. and blowing pure gaseous oxygen into the content at 2 liters/hour under vigorous stirring for 30 hours. On cooling the reaction mixture to room temperature, pale yellow crystals formed as a precipitate in the flask, which were collected by filtration, washed with water and dried to obtain 6.22 g of crystals.

As a result of high-pressure liquid chromatographic analysis of the thus obtained crystals while using Radial Pak ® C₁₈ column (Radial Pak ® is a trade mark by Water Co.) an eluant of a 9:1 mixture of acetonitrile and water and an ultraviolet of 268 nm, it was found that the powdery crystals were a mixture of 80.4% by weight of methyl 2-(2-hydroperoxy-2-propyl)naphthalene-6-carboxylate(the present compound), 16% by weight of the unreacted methyl 2-isopropylnaphthalene-6-carboxylate and 3.6% by weight of the other substance(s).

On mixing the thus obtained powdery crystals with an excess amount of n-hexane by stirring at room temperature, 13.1 g of the present compound (purity: 98%) scarcely containing the starting material was obtained as white powdery crystals. It was confirmed that the crystals were the present compound represented by the formula (I) obtained at a reaction selectivity of 94.1% by mass spectral analysis, infrared absorption analysis, nuclear magnetic resonance spectral analysis, and analysis for peroxide as well as elementary analysis.

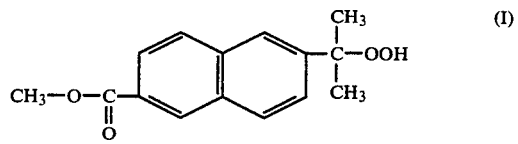

EXAMPLE 2

In the same reaction vessel as in Example 1, 20 g (0.0877 mol) of methyl 2-isopropylnaphthalene-6-carboxylate, 80 ml of water, 0.4 g of azobisisobutyronitrile, 0.64 g of sodium carbonate and 12 mg of cobalt naphthenate were introduced, and peroxidation was carried out while heating the content of the flask at 80° C. and blowing a pure gaseous oxygen into the content at 4 liters/hours under vigorous stirring for 25 hours. On cooling the reaction mixture to room temperature, the thus precipitated powdery crystals were collected by filtration, washed with water and dried to obtain 20.6 g of pale yellow powdery crystals, which was found as the result of high-pressure liquid chromatographic analysis to be a mixture of 72.0% by weight of the present compound, 22.9% by weight of the unreacted starting material and 5.1% by weight of the other substance(s).

By washing the thus obtained crystalline material with an excess amount of n-heptane at room temperature while stirring, 10.5 g of the present compound (purity: 97.5%) was obtained as colourless powdery crystals at a reaction selectivity of 85.1%.

What is claimed is:

1. Methyl 2-(2-hydroperoxy-2-propyl)naphthalene-6-carboxylate represented by the formula(I):

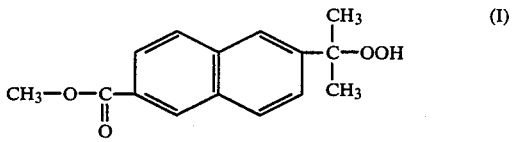

2. A process for producing methyl 2-(2-hydroperoxy-2-propyl)naphthalene-6-carboxylate, comprising reacting methyl 2-isopropylnaphthalene-6-carboxylate with oxygen at a temperature of 70° to 120° C. in an aqueous alkali solution of pH 8 to 13 in the presence of 0.005 to 0.5% by weight of a catalyst comprising a cobalt or manganese salt of an organic acid to the amount of said methyl 2-isopropylnaphthalene-6-carboxylate.

3. A process according to claim 2, wherein the obtained reaction product according to claim 2 is further cooled to precipitate crystals, the thus precipitated crystals are collected and the thus collected crystals are washed with an aliphatic hydrocarbon solvent.

4. A process according to claim 2, wherein said reaction is carried out at a temperature between 80° to 95° C.

5. A process according to claim 2, wherein the amount of said catalyst is 0.02 to 0.1% by weight to the amount of methyl 2-isopropylnaphthalene-6-carboxylate.

6. A process according to claim 2, wherein said reaction is carried out in an aqueous alkali solution of the pH 9 to 12.

* * * * *